(12) United States Patent
Jacobson et al.

(10) Patent No.: US 9,675,280 B2
(45) Date of Patent: Jun. 13, 2017

(54) METHOD AND SYSTEM FOR TRACKING SCORES MADE BY A PLAYER

(71) Applicant: Vibrado Technologies, Inc., Sunnyvale, CA (US)

(72) Inventors: Quinn A. Jacobson, Sunnyvale, CA (US); Cynthia Kuo, Mountain View, CA (US)

(73) Assignee: Vibrado Technologies, Inc., Sunnyvale, CA (US)

( * ) Notice: Subject to any disclaimer, the term of this patent is extended or adjusted under 35 U.S.C. 154(b) by 231 days.

(21) Appl. No.: 14/602,100

(22) Filed: Jan. 21, 2015

(65) Prior Publication Data

US 2015/0202517 A1 Jul. 23, 2015

Related U.S. Application Data

(60) Provisional application No. 61/929,843, filed on Jan. 21, 2014.

(51) Int. Cl.
G06F 19/00 (2011.01)
A61B 5/11 (2006.01)
G06K 9/00 (2006.01)
A61B 5/0488 (2006.01)

(52) U.S. Cl.
CPC ........ *A61B 5/1123* (2013.01); *G06K 9/00342* (2013.01); *A61B 5/0488* (2013.01); *A61B 2503/10* (2013.01); *A61B 2562/0219* (2013.01)

(58) Field of Classification Search
USPC .................................................... 700/90–93
See application file for complete search history.

(56) References Cited

U.S. PATENT DOCUMENTS

| 4,739,329 | A | * | 4/1988 | Ward | G01S 7/003 342/119 |
|---|---|---|---|---|---|
| 8,285,381 | B2 | | 10/2012 | Fahey | |
| 9,014,797 | B2 | | 4/2015 | Shiffman et al. | |
| 9,339,715 | B2 | * | 5/2016 | Luciano, Jr. | A63B 69/3658 |
| 2005/0272496 | A1 | * | 12/2005 | Reinish | A63B 63/00 463/2 |
| 2009/0133499 | A1 | | 5/2009 | Cato | |
| 2010/0020073 | A1 | | 1/2010 | Corazza et al. | |
| 2010/0095773 | A1 | | 4/2010 | Shaw et al. | |
| 2010/0167686 | A1 | | 7/2010 | Pan | |

(Continued)

OTHER PUBLICATIONS

U.S. Appl. No. 14/506,322, Jacobson et al., filed Oct. 3, 2014.
U.S. Appl. No. 14/602,110, Jacobson et al., filed Jan. 21, 2015.

*Primary Examiner* — Ronald Laneau
(74) *Attorney, Agent, or Firm* — Squire Patton Boggs (US) LLP (57) ABSTRACT

Scores made by a player participating in a game can be tracked by using a sensor device coupled to the player to detect when the player attempts to make a score with a ball or other projectile. When a score is made, such as when something enters a goal, it is determined whether the projectile from the player is what made the score so that the score can be properly attributed to the player or another player. Attribution can be based on whether the score occurred within an appropriate time window, which could be computed from data from the sensor device. Attribution can also be based on the use of machine readable identifiers on the projectile, player, and/or goal.

21 Claims, 7 Drawing Sheets

(56) References Cited

U.S. PATENT DOCUMENTS

| | | |
|---|---|---|
| 2010/0262042 A1 | 10/2010 | Kirn |
| 2010/0268080 A1 | 10/2010 | Kirn |
| 2011/0196262 A1 | 8/2011 | McLeod et al. |
| 2011/0221664 A1 | 9/2011 | Chen et al. |
| 2012/0157886 A1 | 6/2012 | Tenn et al. |
| 2012/0188158 A1 | 7/2012 | Tan et al. |
| 2013/0072811 A1 | 3/2013 | Bartol et al. |
| 2013/0266290 A1 | 10/2013 | Sathish |
| 2013/0289434 A1 | 10/2013 | Chou et al. |
| 2014/0150521 A1 | 6/2014 | Jacobson et al. |
| 2014/0163412 A1 | 6/2014 | Jacobson et al. |
| 2015/0100251 A1 | 4/2015 | Solinsky |
| 2015/0375085 A1 | 12/2015 | Molyneux et al. |

\* cited by examiner

METHOD AND SYSTEM FOR TRACKING SCORES MADE BY A PLAYER

CROSS-REFERENCE TO RELATED APPLICATION

This application claims the benefit of U.S. Provisional Application No. 61/929,843, filed Jan. 21, 2014, which is incorporated herein by reference in its entirety and for all purposes.

FIELD

The invention relates, in general to, game and sports equipment, and more particularly, to a method and system that tracks scores made by one or more players.

BACKGROUND

In many sports, there are systems that use technology to detect when a player scores. Some of these systems use cameras while others use electromagnetic signals. Examples include the goal-line technology demonstrated by Cairos Technologies AG and adidas AG for soccer where a sensor module is suspended in a soccer ball, and the ball tracking technology of Hawk-Eye Innovations Ltd. that uses high-speed cameras to determine whether a ball crosses a line. There have also been systems proposed for ice hockey where radio frequency identifiers (RFIDs) are placed in the puck, and sensors are integrated into the goal to detect when the puck enters the goal.

There are sports technologies that monitor players and identify when they are performing certain actions. Examples include a sensor module from FWD-Quattriuum that attaches to a hockey stick.

However, due to fast moving action of many games and the possibility that multiple players are making attempts to score, such as during a practice session, it may be difficult to determine whether the player believed to have made the score truly made the score or if the score was made by another player. Tracking attempts and actual scores is typically performed manually (e.g., visually by a coach or other person) and is therefore an error-prone process. Accordingly, what is needed is a method and system that allows for accurate tracking of scores made by a player.

SUMMARY

Briefly and in general terms, the present invention is directed to a method, system, and computer readable medium for tracking scores made by a player.

In aspects of the present invention, a method comprises detecting an action associated with an attempt to score, the action performed by a player with a projectile, the detecting performed using a sensing device coupled to the player; determining that a goal was made; determining whether the projectile from the player is what made the goal based on a time window in which the projectile was expected to make the goal.

In additional aspects, the method also comprises performing a pre-attempt read operation before or during detecting the action associated with an attempt to score; and matching the projectile to the player based on the pre-attempt read operation.

In additional aspects, the pre-attempt read operation includes reading an identifier of the projectile using a reader coupled to the player, or reading an identifier of the player using a reader coupled to the projectile.

In aspects of the present invention, a system comprises a sensing device configured to sense a physical action associated with an attempt to score performed by a player with a projectile; a goal sensor configured to sense when a goal is made at a first goal; and a processor device communicatively coupled to the sensing device and the goal sensor. The processor device is configured to detect, from the sensing device, the physical action associated with an attempt to score, determine, from the goal sensor, that a goal was made, and determine whether the projectile from the player is what made the goal at the first goal based on a time window in which the projectile was expected to make the goal.

In additional aspects, the system further comprises an ID reader communicatively coupled to the processor device, the ID reader configured to perform a pre-attempt read operation before or during a time when the processor device detects the physical action associated with an attempt to score, and the processor device is configured to match the projectile to the player based on the pre-attempt read operation.

In additional aspects, the system further comprising a projectile identifier secured to the projectile, wherein the ID reader is a player ID reader configured to be secured to the player and is configured to perform the pre-attempt read operation by reading the projectile identifier In additional aspects, the system further comprises a player identifier capable of being secured to the player, wherein the ID reader is a projectile ID reader secured to the projectile and is configured to perform the pre-attempt read operation by reading the player identifier.

In aspects of the present invention, a non-transitory computer readable medium has a stored computer program embodying instructions, which when executed by a computer, causes the computer to tracking scores. The computer readable medium comprises instructions for detecting an action associated with an attempt to score, the action performed by a player with a projectile, the detecting performed using a sensing device coupled to the player; instructions for determining that a goal was made; and instructions determining whether the projectile from the player is what made the goal based on a time window in which the projectile was expected to make the goal.

In additional aspects, the non-transitory computer readable medium further comprises instructions for performing a pre-attempt read operation before or during a time when the action associated with an attempt to score is being detected; and instructions for matching the projectile to the player based on the pre-attempt read operation.

In additional aspects, the instructions for performing the pre-attempt read operation includes instructions for reading an identifier of the projectile using a reader coupled to the player.

In additional aspects, the instructions for performing the pre-attempt read operation includes instructions for reading an identifier of the player using a reader coupled to the projectile.

The features and advantages of the invention will be more readily understood from the following detailed description which should be read in conjunction with the accompanying drawings.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION OF EXEMPLARY EMBODIMENTS

As will be described below, aspects of the invention involve systems and methods that detect when a score is made and also identifies which player made the score. Player identification can is accomplished by pinpointing which player had possession and/or contact immediately before a score is registered. The method and system herein can work for sports or games where the object is to get a gaming projectile into a designated area. The type of gaming projectile and configuration of the designated area will differ depending on the sport or game. For example and without limitation, the gaming projectile can be a ball, puck, dart, etc.

As used herein, the word "goal" refers any type of designated area for scoring. For example and without limitation, a goal can be: an area bounded by rigid poles (e.g., goals in soccer, hockey, and lacrosse games), a hoop (e.g., a basketball hoop), a hole in the ground or a structure (e.g., for golf and miniature golf), and a marked area of the playing surface (e.g., an end zone in American football).

The method and system herein can be used in a game or scrimmage, and can be valuable for practice where multiple players are taking practice shots. With sensors that detect when a player attempts to score, coaches and players (as well as other interested parties) may gain the ability to readily and accurately track the success rates of players during practice and non-practice games. Particularly at team sports practices, there are multiple players and multiple projectiles (e.g., balls, pucks, etc.) attempting to score at the same time. Aspects of the method and system herein can handle multiple projectiles that are concurrently in play.

Although various descriptions herein are made in the context of basketball, it will be appreciated that the method and system herein can be applied to many other sports, games, and activities.

Figure 1:
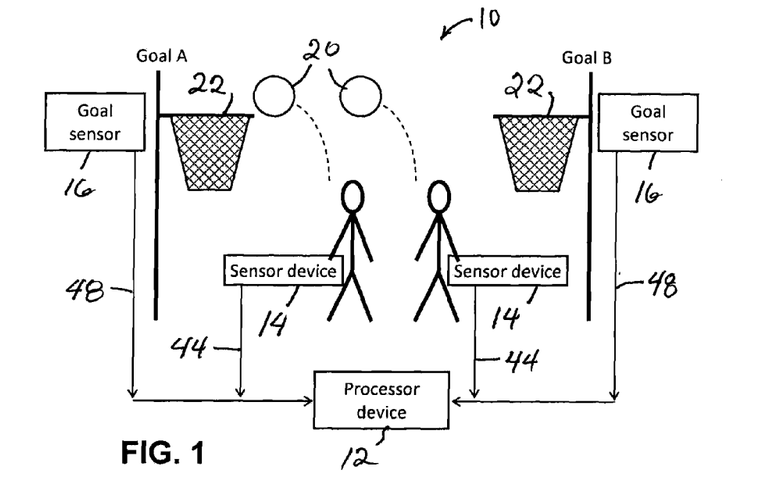
FIG. 1 is a schematic diagram showing an exemplary system in which a sensor device is used to determine whether a player makes an attempt to score.

Referring now in more detail to the exemplary drawings for purposes of illustrating exemplary aspects of the invention, wherein like reference numerals designate corresponding or like elements among the several views, there is shown in FIG. 1 exemplary system 10 for tracking a score of one or more players. Processor device 12 is communicatively coupled to at least one sensor device 14 and at least one goal sensor 16. The number of sensor devices 14 will depend on the number players 18. The number of goal sensors 16 will depend on the number of goals 22. Each player 18 will have only a single sensor device 14 uniquely assigned to him/her, and each goal 22 will have only a single goal sensor 16 uniquely assigned to it.

In FIG. 1, there are two players 18, so there are two sensor devices 14. There are two goals 22 so there are two goal sensors 16. System 10 can be expanded or reduced to include any number of sensor devices and goal sensors. System 10 can be adapted to any game that involves a gaming projectile and a goal. Depending on the type of game, a score is registered when projectile 20 enters, crosses-into, passes through, or touches the goal. In a basketball game, there are multiple players 18, gaming projectile 20 is a basketball, and goal 22 is a hoop at each end of the basketball court. During a practice game, there can be multiple projectiles 20 in play.

In general, a player will perform many different actions during a game. Some actions are not attempts to score. In a basketball game, examples of non-scoring actions include dribbling the basketball and passing the basketball to another player. Some actions are categorized as attempts to score. In a basketball game, examples of scoring attempts include performing a free throw shot, a jump shot, and a layup. Each activity can be uniquely identified by a set of biomechanical and/or mechanical conditions that occur together and/or in a particular sequence. Biomechanical conditions include without limitation: the amount and direction of movement and/or acceleration of a particular part of the player's body; the orientation of a part of the player's body in relation to another part of the player's body; and the type and intensity of muscle contraction of one or more muscles in the player's body. In games where the player uses a gaming implement (e.g., a stick, bat, club, bow, racket, etc.) to maneuver the projectile, mechanical conditions include without limitation: the amount and direction of movement and/or acceleration of one or various parts of the implement; and the orientation of one or various parts of the implement in relation to other parts of the implement and/or in relation to parts of the player's body.

Processor device 12 is configured to receive information from each sensor device 14 and each goal sensor 16 and use the received information to track each player's score. Information from sensor 14 includes data on biomechanical and/or mechanical conditions which characterize the activity being performed by the player. Information from goal sensor 16 includes data on whether a score was registered. Score tracking performed by processor device 12 includes counting the number of times a score is attributed to a player and counting the number of scoring attempts performed by the player. Processor device 12 can then compute the rate of success of the player. Optionally, tracking includes counting the number of scores and attempts for a particular type of scoring attempt (e.g., free throw versus other types of scoring attempts) so that the rate of success for each type of scoring attempt can be computed.

Processor device 12 can be a smart phone, tablet computer, laptop computer, desktop computer, gaming console, or any device that is configured, programmed, or runs software to analyze data received from sensor device 14 and goal sensor 16.

Figure 2:
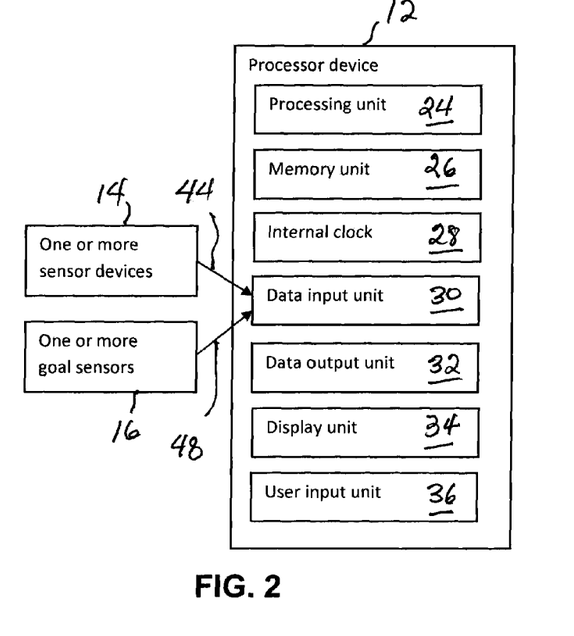
FIG. 2 is a schematic diagram showing an exemplary processor device communicatively coupled to one or more sensor devices of players and one or more goal sensors.

In FIG. 2, exemplary processor device 12 includes processing unit 24 that analyzes data received from sensor device 14 and goal sensor 16. Although processor device 12 is schematically depicted as a single box, it should be understood that various components of processor device 12 can be housed together in a single case or can be housed in separate cases while still being communicatively coupled with each other.

As used herein, "communicatively coupled" means coupled in a way that enables transmission and/or receipt of data. For example and without limitation, devices that are communicatively coupled to each other can be configured to communicate with each other wirelessly (e.g., radio signals, ultrasonic signals, or optical signals) or through electrical or optical cables.

Processing unit 24 can include one or more microprocessors and electronic semiconductor chips. Memory unit 26 includes one or more memory components, e.g., components for volatile and/or non-volatile data storage, for storing data received from sensor device 14 and goal sensor 16. Internal clock 28 enables processor device 12 to keep track of time between a scoring attempt and the occurrence of a score. Data input unit 30 is configured to receive data from sensor device 14 and goal sensor 16. Data input unit 30 may include various components (e.g., antennas, electrical connectors, and data processing circuitry) that allow the data to be received wirelessly (e.g., via radio signals or other electromagnetic radiation) or by wire (e.g., electrical or fiber optic cable).

Optionally, processor device 12 may also includes data output unit 32 that enables processor device 12 to export data to another device. Data output unit 32 may include various components (e.g., antennas, electrical connectors, and data processing circuitry) that allow raw data from sensor device 14 and goal sensor 16 and/or results of data analysis to be transmitted wirelessly or by wire. Processor device 12 may also include display unit 34 that enables processor device 12 to visually display text and/or graphics that represent the data from sensor device 14 and goal sensor 16 and/or results of data analysis. Display unit 34 can be a liquid crystal display screen, light emitting diode display screen, other type of electronic display. Processor device 12 may also include user input unit 36 that allows a person to adjust criteria for detecting scoring attempts and/or edit data received from sensor device 14 and goal sensor 16. Input unit 36 can be a keyboard, touch sensitive screen, microphone, or a remote control button.

Sensor device 14 is uniquely assigned to a particular player 18 in the sense that no two players simultaneously have the same sensor device, and no two sensor devices are simultaneously assigned to the same player. Sensor device 14 is coupled to the player 18. For example, various sensors (referred to below as "player sensors") of sensor device 14 can be (1) secured directly onto the person's skin, (2) secured to an article of clothing or equipment worn by the user so that the sensor is in direct contact with skin, (3) secured to an article of clothing or equipment worn by the user so that the sensor is not in direct contact with skin, and/or (4) secured to a gaming implement (e.g., a stick, bat, club, bow, and racket) uniquely assigned to the player. The type and functional capabilities of a particular sensor will dictate whether the sensor should in contact with the skin or whether the sensor can be at some distance away from the skin.

Figure 3:
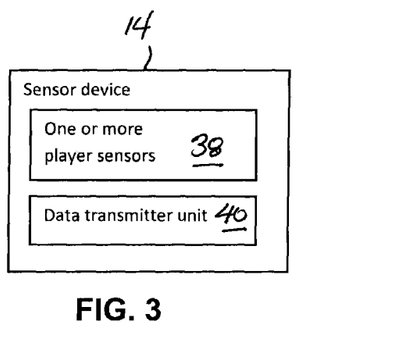
FIG. 3 is a schematic diagram showing an exemplary sensor device of a player.

In FIG. 3, exemplary sensor device 14 includes one or more player sensors 38 and transmitter unit 40. The term "player sensor" refers to a sensor of sensor device 14 to distinguish it from goal sensor 16. As indicated above, player sensor 38 is directly or indirectly coupled to player 18. Transmitter unit 40 may include various components (e.g., antennas, electrical connectors, and data processing circuitry) that allow the data from sensors 38 to be transmitted wirelessly or by wire to processor device 12.

As indicated above, one or more player sensors 38 are located on the player and/or gaming implement (e.g., a stick, bat, club, bow, and racket). For example, player sensors 38 can be distributed at various locations of the player's arm, leg, and/or torso. The location and the total number of sensors will depend upon the type of physical action (e.g., a golf swing, a basketball jump shot, and hockey goal attempt) that is to be detected. Positioning of various sensors at different areas of a person's body is described in U.S. Patent Application Publication No. 2014/0163412, which is incorporated herein by reference.

Player sensors 38 can include an inertial measurement unit (IMU) configured to detect motion of the body. The IMU can be the ones described in U.S. Patent Application Publication No. 2014/0150521 (titled "System and Method for Calibrating Inertial Measurement Units), which is hereby incorporated herein by reference. An IMU is configured to provide information on its orientation, velocity, and acceleration. An IMU may include gyroscopes, accelerometers, and/or magnetometers. A gyroscope is configured to measure the rate and direction of rotation. An accelerometer is configured to measure linear acceleration. A magnetometer (a type of compass) is configured to detect direction relative to magnetic north pole.

Player sensors 38 can include a myography sensor configured to detect whether a particular muscle is being used by the person and optionally how fatigued that muscle is. Myography sensors include sensors configured to provide signals indicative of muscle contraction, such as signals corresponding to electrical impulses from the muscle, signals corresponding to vibrations from the muscle, and/or signals corresponding to acoustics from the muscle, as described in U.S. Patent Application Publication No. 2014/0163412 (titled "Myography Method and System"), which is hereby incorporated herein by reference. Other exemplary myography sensors include those described in U.S. Patent Application Publication Nos. 2010/0262042 (titled "Acoustic Myography Systems and Methods"), 2010/0268080 (titled "Apparatus and Technique to Inspect Muscle Function"), 2012/0157886 (titled "Mechanomyography Signal Input Device, Human-Machine Operating System and Identification Method Thereof"), 2012/0188158 (titled "Wearable Electromyography-based Human-Computer Interface), 2013/0072811 (titled "Neural Monitoring System"), and 2013/0289434 (titled "Device for Measuring and Analyzing Electromyography Signals"), which are hereby incorporated herein by reference.

Myography sensors include without limitation a receiver device configured to detect energy which has passed through the person's body or reflected from the person's body after having been transmitted by a transmitter device. The receiver device need not be in contact with the person's skin. Myography sensors with these types of receiver and transmitter devices are described in co-pending application Ser. No. 14/506,322 (titled "Myography Method and System"), filed Oct. 3, 2014, which is incorporated herein by reference. The type of energy transmitted by the transmitter device and then received by the receiver device includes without limitation sound energy, electromagnetic energy, or a combination thereof, which are used to infer vibrations occurring on the skin surface, below the skin surface, or in the muscle which naturally arise from muscle contraction. For example, the transmitter device can be configured to transmit (and receiver device can be configured to detect) audio signals, which can include acoustic waves, ultrasonic waves, or both. Acoustic waves are in the range of 20 Hz to 20 kHz and include frequencies audible to humans. Ultrasonic waves have frequencies greater than 20 kHz. Additionally or alternatively, transmitter can be configured to transmit (and receiver 16 can be configured to detect) radio waves. For example, radio waves can have frequencies from 300 GHz to as low as 3 kHz. Additionally or alternatively, the transmitter device can be configured to transmit (and receiver device can be configured to detect) infrared light or other frequencies of light. For example, infrared light can have frequencies in the range of 700 nm to 1 mm. These types of energy, after having passed through the person's body or reflected from the person's body, are analyzed by processor device 12 to infer muscle contraction and/or muscle fatigue.

Goal sensor 16 is a device configured to provide an indication of whether projectile 20 made the goal. A statement that a projectile that "makes the goal," "makes the score," "made the goal," or "made the score," means that the projectile has entered, crossed-into, passed through, or touched the goal, or otherwise achieved an objective for registering a score. The appropriate objective for registering a score will vary depending on the activity. In a basketball game, the objective for registering a score is for the projectile to pass through the basketball hoop.

In a basketball game, goal sensor 16 provides an indication of whether basketball 20 has passed through hoop 22. Goal sensor 16 is uniquely assigned to a particular goal 22 in the sense that no two goals are simultaneously assigned to the same goal sensor, and no two goal sensors are simultaneously assigned to the same goals. Goal sensor 16 is physically coupled to goal 22 or located out of contact with goal 22. The way in which goal sensor 16 is oriented relative to goal 22 and optionally secured to goal 22 will depend on the triggering requirements of the goal sensor.

Goal sensor 16 detects and is triggered by a stimulus indicative of a projectile having entered, crossed-into, passed through, or touched the goal, or otherwise achieved an objective for registering a score. The stimulus can be any one or a combination of mechanical action, a magnetic field, ultrasonic waves, other acoustic energy, thermal energy, light, radio frequencies, and other electromagnetic energy. For example, goal sensor 16 can have a lever, and the goal sensor can be coupled to the basketball hoop such that a basketball passing through the hoop will deflect the lever which then actuates an electrical switch. Goal sensor 16 can have a camera that detects when a basketball passes through the hoop. Goal sensor 16 may include a light emitter (e.g., a laser emitter) and a light detector which, in combination, detect when a basketball passes through the hoop. Goal sensor 16 may include a microphone that detects an acoustic signature of a basketball passing through the hoop.

Although the method herein (including aspects associated with FIGS. 4, 5, 8, and 9) are sometimes discussed with reference to systems and hardware described herein, it is to be understood that the method may also be performed with systems configured in other ways.

Figure 4:
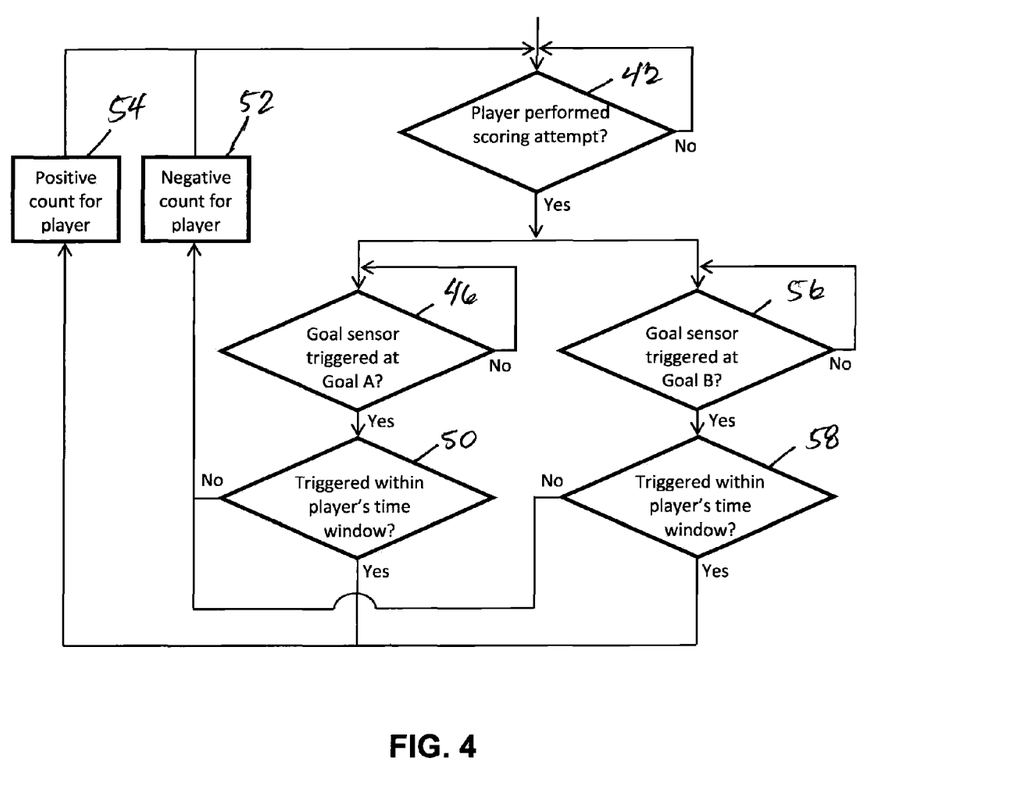
FIG. 4 is a flow diagram showing an exemplary method in which it is determined whether the player performs a scoring attempt.

In FIG. 4, an exemplary method for tracking a score of a player includes checking at block 42 whether a player has performed a scoring attempt. For example processor device 12 can receive player sensor data 44 (FIG. 1) from sensor device 14, analyze measurements of biomechanical and/or mechanical conditions within player sensor data 44 to determine whether the player has formed an action that is associated with an attempt to score. In a basketball game, an action associated with an attempt to score includes a free throw shot. This action can have a unique biomechanical signature in which the player lifts one arm with the elbow and wrist bent in a particular way, followed by movement of the hand in a particular direction and acceleration occurring within a certain period of time. The biomechanical signature may also include contraction of a particular type and intensity of certain muscles in the arm. In a hockey game, an action associated with an attempt to score could be identified at least in part by a mechanical condition of the hockey stick, such as a particular direction and amount of acceleration in the movement of one or more parts of the hockey stick. Processor device 12 may compare the measurements of biomechanical and/or mechanical conditions from sensor data 44 against criteria for many different scoring attempt actions. If one of the criteria is satisfied, then processor device 12 will conclude that the player has performed a scoring attempt.

At block 46 (FIG. 4), the method checks whether a goal sensor has been triggered. For example, processor device 12 can receive trigger signal 48 (FIG. 1) from goal sensor 16 to determine whether a score is to be registered. For example, trigger signal 48 can be an electrical or optical signal that is generated, modified, or returned by goal sensor 16. Trigger signal 48 can be generated, modified, or returned only when projectile 20 has made the goal.

At block 50 (FIG. 4), the method checks whether the goal sensor was triggered within a player's time window. The time window is a period of time in which the projectile of the player was expected to make the goal. The time window may begin from the time when the player performed the scoring attempt, so that the time window represents the period of time after the scoring attempt in which the projectile is expected to make the goal. The time window can be from a fraction of a second to several seconds. For example and without limitation, the appropriate time window can be based on the known height of the player and the known height of the goal. The appropriate time window can be a fixed period of time that does not change between scoring attempts made by the same player. Processor device 12 can compute the appropriate time window, or the time window can be specified by the user of the system.

As used herein, "based on" means based on the elements listed and optionally other elements which are not listed. For example, if feature X is said to be based on elements A and B, then feature X is based at least on elements A and B. Feature X can be based on elements A, B, C, and D.

As a further example, the appropriate time window can be based on the travel path (e.g., low arc versus high arc) and/or velocity of the projectile, and optionally the known heights of the player and the goal. As such, the time window can be different from one scoring attempt to the next scoring attempt. For example, the time window can be from 0.2 second to 0.9 second for a first scoring attempt, and be from 0.5 second to 2 seconds for a subsequent scoring attempt. Processor device 12 can compute the appropriate time window using player sensor data 44 from sensing device 14. Processor device 12 can estimate the travel path (e.g., low arc versus high arc) and/or velocity of projectile 20 based on information within sensor data 44 that represents any one or more of movement of an item (e.g., the player's limb and/or gaming implement) coupled to the sensing device, orientation of the item coupled to the sensing device, acceleration of the item coupled to the sensing device, and intensity of muscle contraction of a muscle adjacent to the sensing device.

In FIG. 4, at block 52 an unsuccessful scoring attempt (e.g., a negative count) will be attributed to the player in the event that the method determines (at block 50) that the goal sensor was not triggered within the appropriate time window. For example, processor device 12 will attribute a scoring attempt to the player but not attribute the score to the player, and then re-compute the success rate of the player as a ratio of the total number of scores attributed to the player and the total number of scoring attempts by the player.

At block 54, a successful scoring attempt (e.g., a positive count) will be attributed to the player in the event that the method determines (at block 50) that the goal sensor was triggered within the appropriate time window. For example, processor device 12 will attribute a scoring attempt to the player and also attribute the score to the player, and then re-compute the success rate of the player as a ratio of the total number of scores attributed to the player and the total number of scoring attempts by the player.

Optionally, the method can take into account the presence of a second goal, as indicated by blocks 56 and 58. Block 56 is performed for Goal B in the same way that block 46 was is performed for Goal A. Block 58 is performed for Goal B in the same way that block 50 was performed for Goal A.

When multiple goal sensors are present, an unsuccessful scoring attempt (e.g., a negative count) will be attributed to the player at block 52 if the method determines that neither the goal sensor at Goal A nor the goal sensor at Goal B was triggered within the appropriate time window. Also, a successful scoring attempt (e.g., a positive count) will be attributed to the player at block 54 if the method determines that either the goal sensor at Goal A or Goal B was triggered within the appropriate time window.

Although FIG. 4 illustrates two goals, the method can be modified to take into account 3 or more goals such that an unsuccessful scoring attempt (e.g., a negative count) will be attributed to the player at block 52 if the method determines that none of the goal sensors was triggered within the appropriate time window.

Figure 5:
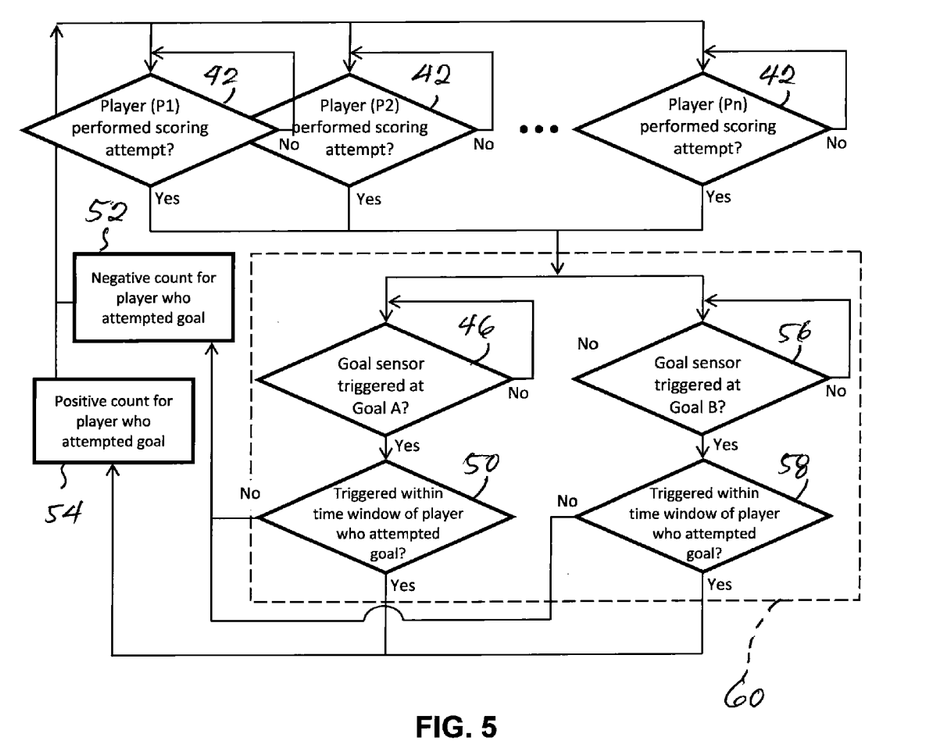
FIG. 5 is a flow diagram showing the method of FIG. 4 augmented for multiple players.

As shown in FIG. 5, the method can take into account the presence of multiple players P1, P2, . . . Pn, where n=total number of players, which can be 2, 4, 10, at least 10, or at least 20. The total number of players may depend on the type of game being played and whether the game is a practice game. There can be only a single projectile or multiple projectiles used in the game.

For each player in FIG. 5, block 42 is performed as described for FIG. 4. For example, processor device 12 can simultaneously monitor player sensor data 44 (FIG. 1) from multiple sensor devices 14 to detect when any player 18 has performed an action associated with an attempt to score, and to identify the particular player that made the attempt. Time verification 60 includes blocks 46 and 50 when the game has only a single goal (Goal A) and further includes blocks 56 and 58 when the game has two goals (Goal A and Goal B). Time verification section 60 can be performed, using an appropriate time window, for each player that made a scoring attempt. As previously discussed, the appropriate time window can be a fixed period of time that does not change, so the same time window can be used for every scoring attempt made by a particular player and/or every scoring attempt by all players. The appropriate time window can be customized based on sensor data 44, and may vary from player to player and/or vary from scoring attempt to scoring attempt depending on the algorithm used by processor device 12.

For each player who made a scoring attempt, an unsuccessful scoring attempt (e.g., a negative count) will be attributed to that player at block 52 if the method determines that none of the goal sensors were triggered within the appropriate time window of that player. Also, a successful scoring attempt (e.g., a positive count) will be attributed to the player at block 54 if the method determines that at least one of the goals was triggered within the appropriate time window of that player.

From the forging discussion, it will be appreciated that the system and method herein can be used to determine which player was last to possess the projectile before a score is registered (i.e., before a goal sensor is triggered). In some sports such as basketball, the player's fingers make direct contact with the projectile. Possession of the projectile need not require direct physical contact between the player and the projectile. In other sports, such as hockey and lacrosse, the player uses a gaming implement to maneuver the projectile.

As described above, aspects of FIGS. 4 and 5 implicitly determine which player was the last person to posses the projectile before a goal sensor is triggered. The determination is implicit in that the method does not use a machine-readable identifier uniquely assigned to the projectile or the player. However, the method can be modified to make the determination explicitly through the use of such a machine-readable identifier. Explicit determination, such as described below, can increase accuracy in tracking scores particularly in games that are played with high projectile speeds, a high number of players, and/or a high number of projectiles.

Figure 6:
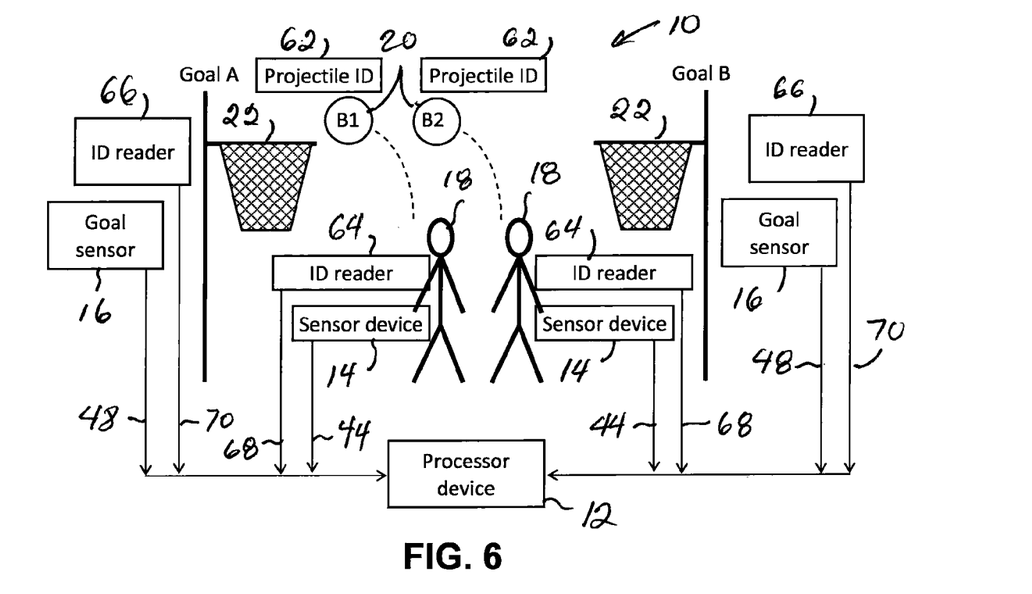
FIG. 6 is a schematic diagram showing an exemplary system in which ID readers on the player and goal are used to match a gaming projectile that registered a score with a player who performed a scoring attempt.

As shown in FIG. 6, system 10 includes all the features of FIG. 1. In addition, system 10 includes projectile identifier 62 for each projectile 20, player ID reader 64 for each player 18, and goal ID reader 66 for each goal 22. Player ID reader 64 and goal ID reader 66 are devices capable of reading projectile identifier 62. Each projectile identifier 62 is different from all other projectile identifiers that might also be in the game. Thus, each projectile identifier 62 distinguishes its projectile from all other projectiles that might also be in the game.

Player ID reader 64 enables processor device 12 to determine the identity of the projectile possessed by player 18 before or during the time the player performs an action associated with a scoring attempt. This can be accomplished by player ID reader 64 performing a "pre-attempt" read operation on projectile identifier 62 before or during the scoring attempt. The result of the pre-attempt read operation (e.g., a serial number, code, or other indicia that uniquely identifies the projectile of the player) is transmitted as ID signal 68, which is received by processor device 12. Processor device 12 assigns that particular projectile to the player.

In FIG. 6, goal ID reader 66 enables processor device 12 to check whether the projectile which triggered goal sensor 16 matches the player that performed a scoring attempt. This can be accomplished by goal ID reader 66 performing a "post-attempt" read operation on projectile identifier 62 after the scoring attempt. The result of the post-attempt read operation (e.g., a serial number, code, or other indicia that uniquely identifies the projectile that triggered goal sensor 16) is transmitted as ID signal 70, which is received by processor device 12. Processor device 12 uses information in ID signal 70 to correlate the player who performed the scoring attempt to the projectile which made the goal. The score is attributed to the player who attempted the score if: (1) the goal sensor 16 was triggered within the appropriate time window, and (2) the serial number, code, etc. from the post-attempt read operation is the same as the serial number, code, etc. from the pre-attempt read operation.

Projectile identifier 62 is a machine-readable identifier. Projectile identifier 62 can include a radio frequency identification (RFID) chip having a serial number or electromagnetic signature that distinguishes the projectile from all other projectiles in the game. Projectile identifier 62 can include an ultrasonic broadcasting device that emits an ultrasonic signal that distinguishes the projectile from all other projectiles in the game. Projectile identifier 62 can include an infrared broadcasting device that emits an infrared light signal that distinguishes the projectile from all other projectiles in the game. Projectile identifier 62 can include a graphical marker, such as a bar code or 2-dimensional bar code, that distinguishes the projectile from all other projectiles in the game.

Still referring to FIG. 6, player ID reader 64 is coupled to player 18. For example, player ID reader 64 can be (1) secured in contact with the player, (2) secured to an article of clothing or equipment worn by player, or (3) secured to a gaming implement (e.g., a stick, bat, club, bow, and racket) uniquely assigned to the player.

As used herein, the word "coupled" encompasses direct and indirect attachment. A device that is coupled to an item can be physically attached to the item directly or physically attached to the item by an intervening structure between the device and the item. As used herein, the word "secured" encompasses attached directly to, embedded within, mounted on, printed on, and forming an integral part of A device that is secured to an item can be attached directly to the item, embedded within the item, mounted on the item, and form an integral part of the item.

Player ID reader 64 is configured to send identification signal 68 to processor device 12. Identification signal 68 includes a serial number, code, or other indicia that uniquely identifies the projectile that was used by player 18 when performing a scoring attempt.

As shown in FIG. 6, each goal has its own goal ID reader 66. Goal ID reader 66 is configured to send identification signal 70 to processor device 12. Identification signal 70 includes a serial number, code, or other indicia that uniquely identifies the projectile that triggered goal sensor 16. Like goal sensor 16, goal ID reader 66 can be physically coupled to the goal or it can be located out of contact with the goal. The way in which goal ID reader 66 is oriented relative to goal 22 and optionally secured to goal 22 will depend on the functional capabilities of the goal ID reader.

The type and functional capabilities of player ID reader 64 and goal ID reader 66 will depend upon the type of projectile identifier 62. For example, ID readers 64 and 66 can include a radio frequency transmitter-receiver configured broadcast a signal and read a response from a nearby RFID chip of projectile 20. ID readers 64 and 66 can include an ultrasonic receiver device that detects an ultrasonic signal from an ultrasonic broadcasting device of projectile 20. ID readers 64 and 66 can include an optical sensor configured to detect an infrared light signal emitted by an infrared broadcasting device of projectile 20. ID readers 64 and 66 can include an optical scanner configured to emit light toward a graphical marker on projectile 20 and distinguish the graphical marker from the graphical markers of other projectiles.

Goal ID reader 66 and goal sensor 16 are schematically illustrated as separate boxes. In some aspects, goal ID reader 66 and goal sensor 16 can be integrated into a single apparatus which performs both the function of goal sensor and ID reader.

Figure 7:
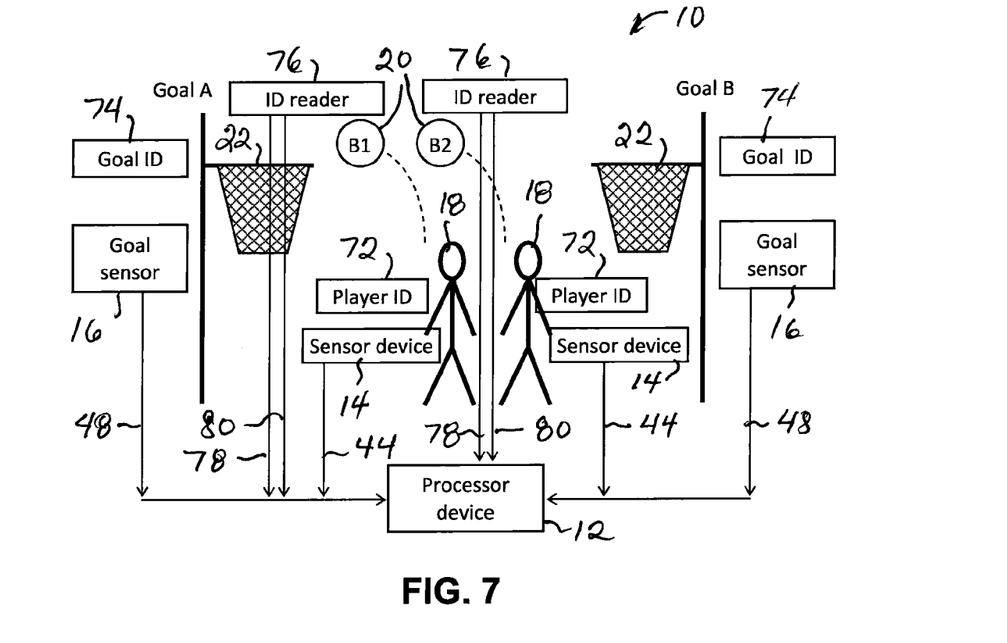
FIG. 7 is a schematic diagram showing an exemplary system in which ID readers on projectiles are used to match a projectile that registered a score with a player who performed a scoring attempt.

As shown in FIG. 7, system 10 can be modified so that the ID reader is assigned to projectile 20 instead of player 18 and goal 22. Here, system 10 includes all the features of that in FIG. 1. In addition, system 10 includes player identifier 72 for each player 18, goal identifier 74 for each goal 22, and projectile ID reader 76. Projectile ID reader 76 is a device capable of reading player identifier 72 and goal identifier 74. Projectile ID reader 76 is secured to projectile 20.

Player identifier 72 and goal identifier 74 can be the same type of identifier described for projectile identifier 62 of FIG. 6. Projectile ID reader 76 can be the same type of reader described for player ID reader 64 of FIG. 6. Optionally, each player identifier 72 is different from all player identifiers that could be in the game. Optionally, each goal identifier 74 is different from all other goal identifiers that could be in the game.

Player identifier 72 enables processor device 12 to determine which projectile was used by player 18 before or during the time the player performs an action associated with a scoring attempt. This can be accomplished by projectile ID reader 76 performing a "pre-attempt" read operation on player identifier 72 before or during the time the player performs the action. The result of the pre-attempt read operation (e.g., a serial number, code, or other indicia that uniquely identifies the projectile and, optionally, the player) is transmitted as ID signal 78, which is received by processor device 12. When the player performs a scoring attempt with a projectile, processor device 12 assigns that particular projectile to the player.

In FIG. 7, goal identifier 74 enables processor device 12 to check whether the projectile which triggered goal sensor 16 matches the player that performed a scoring attempt. This can be accomplished by projectile ID reader 76 performing a "post-attempt" read operation on goal identifier 74 after the scoring attempt. The result of the post-attempt read operation (e.g., a serial number, code, or other indicia that uniquely identifies the projectile and, optionally, the goal) is transmitted as ID signal 80, which is received by processor device 12. Processor device 12 uses information in ID signal 80 to correlate the player who performed the scoring attempt to the projectile that triggered goal sensor 16. The score is attributed to the player if processor device 12 receives both ID signal 78 (which corresponds to the player who performed the scoring attempt) and ID signal 80 (which corresponds to a score that occurred with an appropriate time window after the scoring attempt) from the same projectile.

Figure 8:
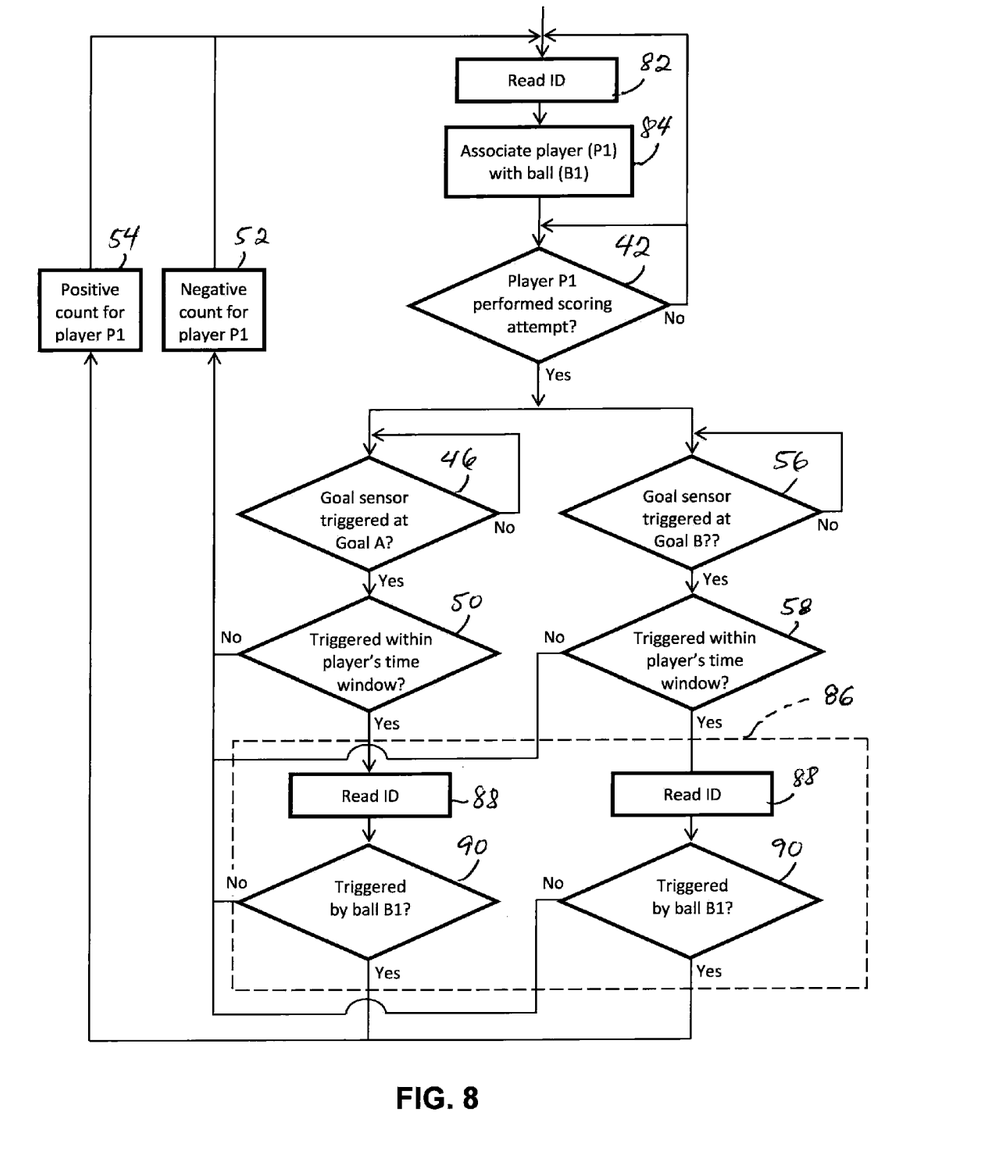
FIG. 8 is a flow diagram showing an exemplary method in which ID verification is performed.

In FIG. 8, an exemplary method performs a pre-attempt read operation at block 82, and the result of pre-attempt read operation 82 is used to associate the player with the projectile at block 84. For example, player ID reader 64 (FIG. 6) can perform pre-attempt read operation 82 on projectile identifier 62 before or during the time the player performs the action. The result of the pre-attempt read operation (e.g., a serial number, code, or other indicia that uniquely identifies the projectile used by the player) is transmitted as ID signal 68, which is received by processor device 12. At block 84, processor device 12 assigns that particular projectile to the player.

Alternatively or additionally, projectile ID reader 76 (FIG. 7) can perform pre-attempt read operation 82 on player identifier 72 before or during the time the player performs the scoring attempt, and the result (e.g., a serial number, code, or other indicia that uniquely identifies the projectile and, optionally, the player in possession of the projectile) is transmitted as ID signal 78, which is received by processor device 12. At block 84, processor device 12 assigns that particular projectile to the player.

After block 84 (FIG. 8), the method may proceed as in FIG. 4 with the addition of ID validation 86 performed for each goal sensor that was triggered within the appropriate time window of the player. In ID validation 86, a post-attempt read operation is performed at block 88. The result of post-attempt read operation 84 is used to try to match the player who performed the scoring attempt to the projectile that made the goal. At block 90, processor device 12 determines whether the goal sensor was triggered by the projectile associated with the player who performed a scoring attempt.

Figure 9:
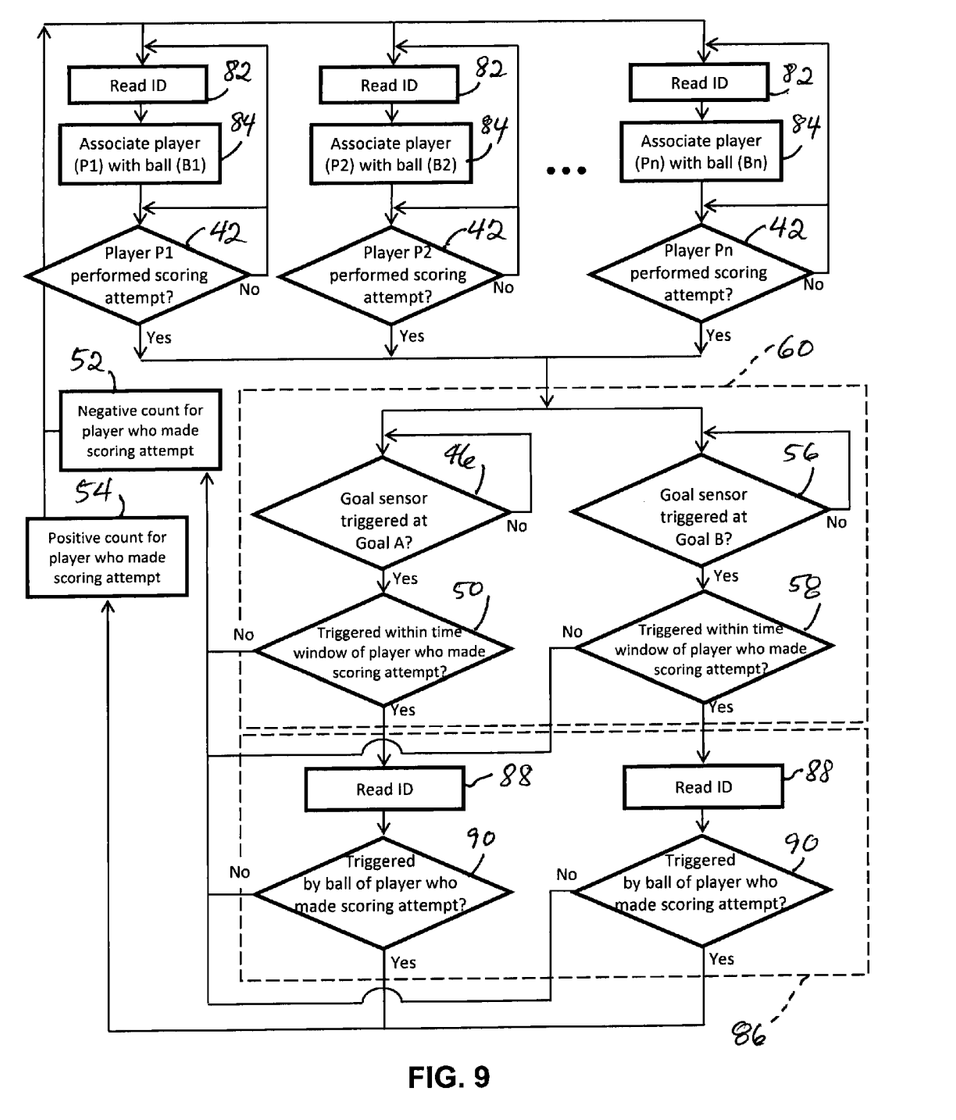
FIG. 9 is a flow diagram showing the method of FIG. 8 augmented for a multiple players.

As shown in FIG. 9, the method of FIG. 8 can be modified to accommodate any number of players: P1, P2, . . . Pn, where n=total number of players, which can be 2, 4, 10, at least 10, or at least 20. The total number of players may depend on the type of game being played and whether the game is a practice game. There can be only a single projectile or multiple projectiles used in the game.

For each player in FIG. 9, blocks 82, 84, and 74 are performed as described for FIG. 8. For example, processor device 12 can simultaneously monitor player ID reader 64 (FIG. 6) or projectile ID reader 76 (FIG. 7). Time verification 60 includes blocks 46 and 50 when the game has only a single goal (Goal A) and further includes blocks 56 and 58 when the game has two goals (Goal A and Goal B). Time verification 60 can be performed, using an appropriate time window, for each player that made a scoring attempt. As previously discussed, the appropriate time window can be a fixed period of time that does not change, so the same time window can be used for every scoring attempt made by a particular player and/or every scoring attempt by all players. The time window may vary from player to player and/or vary from scoring attempt to scoring attempt. ID validation 86 is performed for each goal sensor that is triggered within the appropriate time window. ID validation 86 includes post-read operation 88 and determination 90 of whether the goal sensor was triggered by a projectile associated with the player who performed the scoring attempt.

For each player who made a scoring attempt, an unsuccessful scoring attempt (e.g., a negative count) will be attributed to that player at block 52 if: (1) none of the goal sensors were triggered within the appropriate time window for that player, or (2) none of the goal sensors, which were triggered within the appropriate time window, were triggered by a projectile associated with that player.

For each player who made a scoring attempt, a successful scoring attempt (e.g., a positive count) will be attributed to the player at block 54 if the method determines that at least one of the goal sensors was triggered within the appropriate time window of that player by a projectile associated with that player.

As mentioned above, player sensor device 14 may include a plurality of player sensors 38. Player sensors 38 can be mounted on a garment or other article configured to be worn on the person's body while playing the game. Examples of garments include without limitation shirts, arm sleeves, vests, leggings, girdles, head caps, and gloves. Other articles configured to be worn on the person's body include without limitation braces, bands (e.g., for wrist, arm, leg, chest, or head), shoes, helmets, face masks, and other protective equipment such as shin guards, pads (e.g., for knee, elbow, or shoulder), etc.

Figure 10:
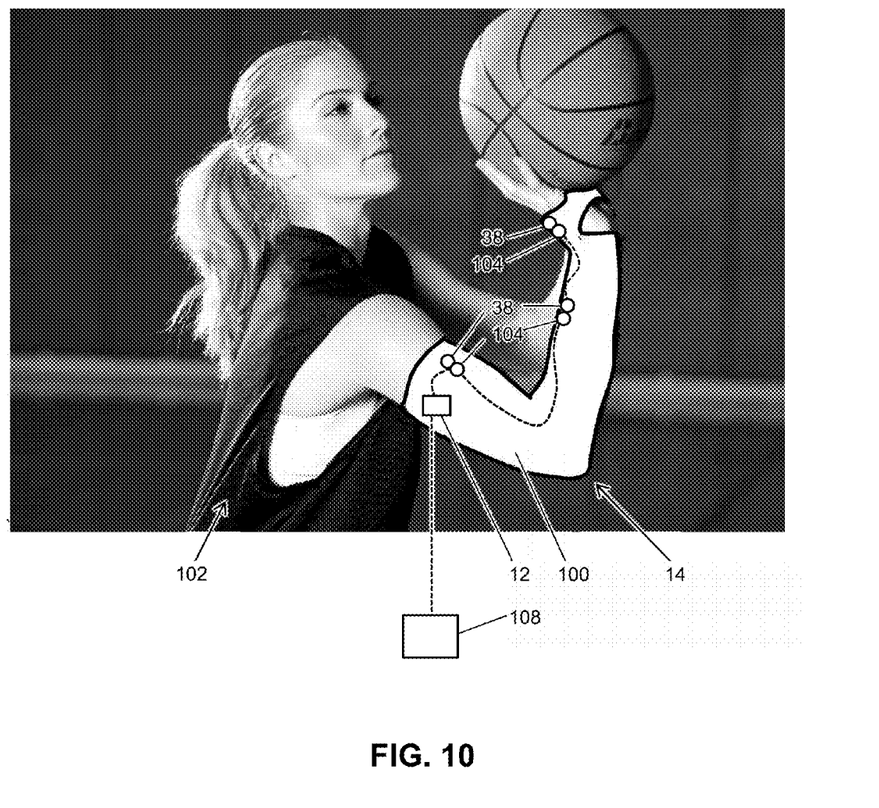
FIG. 10 is a photograph showing a person wearing an exemplary sensor device used to determine whether the player makes an attempt to score, which can be used in combination with aspects described for FIGS. 1-9.

In FIG. 10, sensor device 14 includes player sensors 38 that are mounted on fabric sleeve 100 which can be worn while playing a sport such as basketball. Sensor device 14 is a sensor/sleeve combination, referred to as training sleeve, which can provide a basketball player with feedback on jump shots and free throws.

Player sensors 38 attached to fabric sleeve 100 detect the primary shooting arm of athlete 102. Sleeve 110 mounts player sensors 38 to the arm of athlete 102. Player sensors 38 enable processor device 12 to detect when athlete 102 makes a shot (i.e., scoring attempt) toward a basketball hoop (as opposed to another maneuver, such as dribbling the ball) and to analyze the form of the scoring attempt. Athlete 102 can receive immediate feedback through audio and visual indicators 104 coupled to player sensors 38. Indicators 104 can include lights (e.g., light emitting diodes or lamps) and/or speakers or other device configured to generate a sound. When the athlete's form is incorrect or undesirable, indicators 104 emit a light and/or sound to indicate how to improve future scoring attempts. Athlete 102 may also track her performance and compare it to that of teammates using a smartphone app (e.g. a software application program).

Training sleeve 14 includes three player sensors 38: one on the back of the hand, one on the forearm, and one on the upper arm. Each player sensor 38 comprises a 3-axis accelerometer, a 3-axis gyroscope, and a 3-axis compass which, in combination, accurately track rotation and motion in space using algorithms. Player sensors 38 are communicatively coupled to processor device 12 which applies the algorithm to sensor data 44. Player sensors 38 are sampled by processor device 12 at around 200 times per second. From sensor data 44, processor device 12 can determine the current rotation of the shoulder, elbow, and wrist.

Processor device 12 uses sensor data from sensors 38 to detect when the athlete performs a scoring attempt and analyzes whether the action was performed with good or bad form. The detection of a scoring attempt and analysis are performed using algorithms running in processor device 12. The scoring attempt is broken down into many measurable parts, generally measurements in time and space. Measurements can include without limitation joint angles, acceleration, rotation, and direction of movement. The reference or criteria for "good form" is based on a set of constraints of these measurable parts. The reference or criteria for good form can be configured from the smartphone app to personalize for a particular athlete.

As indicated above, athlete 102 can get immediate feedback through audio and visual indicia from indicators 104. Processor device 12 causes indicators 104 to provide immediate feedback after a scoring attempt by either playing a sequence of tones and/or by speaking to the player to provide guidance. Lights of indicators 104 can be lit up to indicate what type of mistake may have been made.

Processor device 12 can communicate to device 108 using Bluetooth or other wireless communication protocol. Device 108 can be a smartphone or other mobile electronic computing device, a laptop computer, a desktop computer, or device similar to processor device 12. This can allow all sensor data 44 from training sleeve 14 to be uploaded into a cloud storage environment. Further analysis as well as tracking of performance over time can be performed either on the smartphone or in the cloud or both. The smartphone can also be used to personalize settings for players, as well as to update the software and algorithms running on processor device 12.

In any of the aspects described in association with FIGS. 1-10, processor device 12, can be capable of executing, in accordance with a computer program stored on a non-transitory computer readable medium, any one or a combination of the steps and functions described above for tracking scores. The non-transitory computer readable medium may comprise instructions for performing any one or a combination of the steps and functions described herein. Processing unit 24 (FIG. 2) and/or memory unit 26 may include the non-transitory computer readable medium. Examples of a non-transitory computer readable medium includes without limitation non-volatile memory such as read only memory (ROM), programmable read only memory, and erasable read only memory; volatile memory such as random access memory; optical storage devices such as compact discs (CDs) and digital versatile discs (DVDs); and magnetic storage devices such as hard disk drives and floppy disk drives.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method for tracking scores made by a player, the method comprising:
    detecting an action associated with an attempt to score, the action performed by a player with a projectile, the detecting performed using a sensing device coupled to the player;
    determining that a goal was made;
    determining whether the projectile from the player is what made the goal based on a time window in which the projectile was expected to make the goal; and
    performing a pre-attempt read operation before or during detecting the action associated with an attempt to score; and
    matching the projectile to the player based on the pre-attempt read operation.

2. The method of claim 1, wherein the sensing device is either secured to the player, secured to an article worn by the player, or secured to an implement for propelling the projectile.

3. The method of claim 1, wherein detecting the action associated with an attempt to score includes receiving a measurement taken by the sensing device of one or more of movement of an item coupled to the sensing device, orientation of an item coupled to the sensing device, acceleration of an item coupled to the sensing device, and muscle contraction of a muscle adjacent to the sensing device.

4. The method of claim 1, wherein:
    the sensing device includes a plurality of player sensors secured to the player,
    each player sensor is secured at a location different from that of the other player sensors,
    detecting the action associated with an attempt to score includes receiving a data signal from each player sensor, and
    the data signal is representative of one or more of movement of a portion of the player's body secured to the player sensor, orientation of a portion of the player's body secured to the player sensor, acceleration of a portion of the player's body secured to the player sensor, or muscle contraction of a muscle adjacent to the player sensor.

5. The method of claim 1, wherein detecting the action associated with an attempt to score includes applying criteria to information received from sensing device, the criteria including a requirement for one or more of movement, orientation, acceleration, and muscle contraction.

6. The method of claim 1, wherein determining that the goal was made includes using a goal sensor that detects a stimulus indicative that the goal was made.

7. The method of claim 1, wherein determining that the goal was made includes receiving a trigger signal initiated by any one or more of a mechanical movement, magnetism, acoustic energy, and electromagnetic radiation.

8. The method of claim 1, wherein determining whether the projectile is what made the goal includes computing the time window using information from the sensing device coupled to the player, and the information represents any one or more of movement of an item coupled to the sensing device, orientation of an item coupled to the sensing device, acceleration of an item coupled to the sensing device, and muscle contraction of a muscle adjacent to the sensing device.

9. The method of claim 1, wherein determining whether the projectile is what made the goal includes concluding that the projectile is what made the goal on condition that the goal was made within the time window.

10. The method of claim 1, wherein determining whether the projectile is what made the goal includes concluding that the projectile is not what made the goal on condition that the goal was made outside of the time window.

11. The method of claim 1, further comprising:
    determining that a second goal was made; and
    determining whether the projectile is what made the second goal based on the time window.

12. The method of claim 1, further comprising:
    detecting a second action associated with an attempt to score, the second action performed by a second player with a second projectile, the detecting performed using a second sensing device coupled to the second player; and
    determining whether the second projectile is what made the goal based on a second time window in which the second projectile was expected to make the goal.

13. The method of claim 1, wherein the pre-attempt read operation includes reading an identifier of the projectile using a reader coupled to the player, or reading an identifier of the player using a reader coupled to the projectile.

14. The method of claim 1, wherein determining whether the projectile is what made the goal includes concluding that the projectile is what made the goal after the following: determining that the goal was made within the time window, and determining that what made the goal matches the player based on the pre-attempt read operation.

15. The method of claim 1, wherein determining whether the projectile is what made the goal includes concluding that the projectile is not what made the goal after the following: determining that the goal was made within the time window, and determining that what made the goal does not match the player based on the pre-attempt read operation.

16. The method of claim 1, further comprising:
performing a post-attempt read operation after detecting the action associated with an attempt to score; and
checking whether what made the goal matches the player based on the pre-attempt read operation and the post-attempt read operation.

17. The method of claim 16, wherein the post-attempt read operation includes reading an identifier of the projectile using a reader assigned to the goal, or reading an identifier of the goal using a reader secured to the projectile.

18. The method of claim 1, further comprising:
determining that a second goal was made; and
concluding that the projectile is what made the second goal after the following: determining that the second goal was made within the time window, and determining that what made the second goal matches the player based on the pre-attempt read operation and, if depending from claim 16 or 17, the post-attempt read operation.

19. The method of claim 1, further comprising:
detecting a second action associated with an attempt to score, the second action performed by a second player with a second projectile, the detecting performed using a second sensing device coupled to the second player;
performing a pre-attempt read operation for the second player before or during detecting the second action;
matching the second projectile to the second player based on the pre-attempt read operation for the second player;
performing a post-attempt read operation after detecting the second action; and
concluding that the second projectile is what made the goal after the following: determining that the goal was made within the second time window, and determining that what made the goal matches the second player based on the pre-attempt and post-attempt read operations for the second player.

20. A system for tracking scores made by a player, the system comprising:
a sensing device configured to sense a physical action associated with an attempt to score performed by a player with a projectile;
a goal sensor configured to sense when a goal is made at a first goal;
a processor device communicatively coupled to the sensing device and the goal sensor, the processor device configured to
detect, from the sensing device, the physical action associated with an attempt to score,
determine, from the goal sensor, that a goal was made, and
determine whether the projectile from the player is what made the goal at the first goal based on a time window in which the projectile was expected to make the goal; and
an ID reader communicatively coupled to the processor device, the ID reader configured to perform a pre-attempt read operation before or during a time when the processor device detects the physical action associated with an attempt to score, and the processor device is configured to match the projectile to the player based on the pre-attempt read operation.

21. A non-transitory computer readable medium having a stored computer program embodying instructions, which when executed by a computer, causes the computer to track scores, the computer readable medium comprising:
instructions for detecting an action associated with an attempt to score, the action performed by a player with a projectile, the detecting performed using a sensing device coupled to the player;
instructions for determining that a goal was made;
instructions determining whether the projectile from the player is what made the goal based on a time window in which the projectile was expected to make the goal;
instructions for performing a pre-attempt read operation before or during a time when the action associated with an attempt to score is being detected; and
instructions for matching the projectile to the player based on the pre-attempt read operation.

* * * * *